(12) United States Patent
Donaldson (10) Patent No.: US 11,324,609 B2
(45) Date of Patent: May 10, 2022

(54) SPINAL IMPLANT INSERTION TOOL

(71) Applicant: JWD Products, LLC, Indianapolis, IN (US)

(72) Inventor: Jill Donaldson, Indianapolis, IN (US)

(73) Assignee: JWD Products, LLC, Indianapolis, IN (US)

( * ) Notice: Subject to any disclaimer, the term of this patent is extended or adjusted under 35 U.S.C. 154(b) by 140 days.

(21) Appl. No.: 16/947,187

(22) Filed: Jul. 22, 2020

(65) Prior Publication Data

US 2020/0345516 A1 Nov. 5, 2020

Related U.S. Application Data

(63) Continuation-in-part of application No. 15/958,629, filed on Apr. 20, 2018, now Pat. No. 10,932,922.

(51) Int. Cl.
*A61F 2/46* (2006.01)
*A61F 2/44* (2006.01)
*A61B 17/70* (2006.01)

(52) U.S. Cl.
CPC .......... *A61F 2/4611* (2013.01); *A61F 2/4455* (2013.01)

(58) Field of Classification Search
CPC .... A61F 2/4601; A61F 2/4603; A61F 2/4611; A61F 2/44; A61F 2/4455; A61F 2/442; A61B 17/7074; A61B 17/7059
USPC ............ 606/99, 86 R, 279; 623/17.11–17.16
See application file for complete search history.

(56) References Cited

U.S. PATENT DOCUMENTS

| | | | |
|---|---|---|---|
| 5,616,144 A | 4/1997 | Yapp et al. | |
| 5,800,550 A | 9/1998 | Sertich | |
| 5,885,299 A | 3/1999 | Winslow et al. | |
| 5,951,564 A * | 9/1999 | Schroder | A61F 2/4607 606/100 |
| 6,004,326 A | 12/1999 | Castro et al. | |
| 6,059,790 A | 5/2000 | Sand et al. | |
| 6,083,225 A | 7/2000 | Winslow | |
| 6,436,140 B1 | 8/2002 | Liu et al. | |
| 6,478,800 B1 | 11/2002 | Fraser et al. | |
| 6,478,801 B1 | 11/2002 | Ralph et al. | |
| 6,572,619 B2 | 6/2003 | Santilli | |

(Continued)

OTHER PUBLICATIONS

Amedica. Valeo C Interbody Fusion Device, [online], [retrieved on Sep. 29, 2014], Retrieved from the Internet <URL:http://www.amedica.com/product_types/valeo_interbody_fusion_devices/valeo_c_interbody_fusion_device/>.

(Continued)

*Primary Examiner* — Jessica Weiss
(74) *Attorney, Agent, or Firm* — Woodard, Emhardt, Henry, Reeves & Wagner, LLP (57) ABSTRACT

A spinal implant insertion tool includes a handle portion formed by the proximal ends of a first prong and second prong and an attachment portion formed by the distal ends of the first prong and the second prong. The spinal implant insertion tool also includes a hinged portion positioned between the handle portion and the attachment portion where the first and second prongs are coupled by a hinge. A first attachment section includes first connectors for holding a spinal plate. A second attachment portion includes second connectors for holding a spinal cage. The first prong includes an oblique portion so that it is nonlinear, while the second prong is linear, so that the hinge is offset from the spinal cage and spinal plate held by the spinal implant insertion tool.

20 Claims, 9 Drawing Sheets

(56) References Cited

U.S. PATENT DOCUMENTS

| | | |
|---|---|---|
| 6,755,841 B2 | 6/2004 | Fraser et al. |
| 6,805,716 B2 | 10/2004 | Ralph et al. |
| 6,855,151 B2 | 2/2005 | Ralph et al. |
| 6,863,673 B2* | 3/2005 | Gerbec .................. A61F 2/447 606/99 |
| 6,976,988 B2 | 12/2005 | Ralph et al. |
| 7,074,221 B2 | 7/2006 | Michelson |
| 7,326,248 B2 | 2/2008 | Michelson |
| 7,695,478 B2 | 4/2010 | Ralph et al. |
| 7,846,207 B2 | 12/2010 | Lechmann et al. |
| 8,057,548 B2 | 11/2011 | Abernathie et al. |
| 8,123,757 B2 | 2/2012 | Zalenski et al. |
| RE43,317 E | 4/2012 | Fraser et al. |
| 8,187,333 B2 | 5/2012 | Mayer |
| 8,257,439 B2 | 9/2012 | Zeegers |
| 8,257,443 B2 | 9/2012 | Kamran et al. |
| 8,262,666 B2 | 9/2012 | Baynham et al. |
| 8,277,510 B2 | 10/2012 | Kleiner |
| 8,343,164 B2 | 1/2013 | Wallenstein et al. |
| 8,343,219 B2 | 1/2013 | Allain et al. |
| 8,348,958 B2 | 1/2013 | Ralph et al. |
| 8,361,155 B2 | 1/2013 | Lambrecht et al. |
| 8,377,072 B2 | 2/2013 | Stad et al. |
| 8,425,569 B2 | 4/2013 | O'Farrell et al. |
| 8,480,716 B2 | 7/2013 | Perrow et al. |
| 8,491,643 B2 | 7/2013 | Lauryssen et al. |
| 8,496,709 B2 | 7/2013 | Schell et al. |
| 8,523,945 B1 | 9/2013 | Wensel |
| 8,579,909 B2 | 11/2013 | Burkus et al. |
| 8,636,746 B2 | 1/2014 | Jimenez et al. |
| 8,641,743 B2 | 2/2014 | Michelson |
| 8,641,766 B2 | 2/2014 | Donner et al. |
| 8,657,832 B2 | 2/2014 | Purcell et al. |
| RE44,835 E | 4/2014 | Fraser et al. |
| 8,685,031 B2 | 4/2014 | Kleiner et al. |
| 8,685,100 B2 | 4/2014 | Jodaitis et al. |
| 8,685,104 B2 | 4/2014 | Lee et al. |
| 8,709,088 B2 | 4/2014 | Kleiner et al. |
| 8,715,354 B2 | 5/2014 | Lechmann et al. |
| 8,715,355 B2 | 5/2014 | Kleiner |
| 8,771,284 B2 | 7/2014 | Rashbaum et al. |
| 8,808,305 B2 | 8/2014 | Kleiner |
| 8,828,018 B2 | 9/2014 | Ragab et al. |
| 8,945,227 B2 | 2/2015 | Kirschman |
| 8,998,920 B2 | 4/2015 | Berry et al. |
| 9,011,500 B2 | 4/2015 | Suh et al. |
| 9,023,109 B2 | 5/2015 | Weiland |
| 9,060,877 B2 | 6/2015 | Kleiner |
| 9,173,694 B2 | 11/2015 | Kleiner |
| 9,186,193 B2 | 11/2015 | Kleiner et al. |
| 9,277,943 B2 | 3/2016 | Holly et al. |
| 9,439,782 B2 | 9/2016 | Kleiner |
| 9,486,250 B2 | 11/2016 | Altarac et al. |
| 9,622,878 B2 | 4/2017 | Grotz |
| 9,629,729 B2 | 4/2017 | Grimberg, Jr. et al. |
| 9,848,998 B2 | 12/2017 | Moskowitz et al. |
| 9,861,494 B2 | 1/2018 | Grotz |
| 2002/0165550 A1* | 11/2002 | Frey .................. A61B 17/1671 606/85 |
| 2004/0186483 A1 | 9/2004 | Bagby |
| 2004/0193174 A1 | 9/2004 | Bagby |
| 2005/0015094 A1* | 1/2005 | Keller .................. A61F 2/4611 606/99 |
| 2005/0015095 A1* | 1/2005 | Keller .................. A61F 2/4611 606/99 |
| 2006/0276793 A1 | 12/2006 | Berry |
| 2007/0123903 A1 | 5/2007 | Raymond et al. |
| 2007/0123985 A1* | 5/2007 | Errico .................. A61B 90/94 623/17.11 |
| 2008/0140085 A1 | 6/2008 | Gately et al. |
| 2008/0154382 A1* | 6/2008 | de Villiers ............ A61F 2/4425 623/17.16 |
| 2009/0182383 A1 | 7/2009 | Prybyla et al. |
| 2009/0234455 A1* | 9/2009 | Moskowitz .............. A61F 2/447 623/17.11 |
| 2009/0287257 A1 | 11/2009 | Hagen |
| 2011/0196494 A1 | 8/2011 | Yedlicka et al. |
| 2012/0078371 A1 | 3/2012 | Gamache et al. |
| 2012/0179259 A1* | 7/2012 | McDonough ......... A61F 2/4455 623/17.16 |
| 2012/0330424 A1 | 12/2012 | Zeegers |
| 2013/0150968 A1 | 6/2013 | Dinville et al. |
| 2013/0166029 A1 | 6/2013 | Dinville et al. |
| 2013/0226300 A1 | 8/2013 | Chataigner et al. |
| 2014/0114413 A1 | 4/2014 | Allain et al. |
| 2014/0163684 A1 | 6/2014 | Donner et al. |
| 2014/0180417 A1 | 6/2014 | Bergey |
| 2015/0100126 A1* | 4/2015 | Melkent ................ A61F 2/4611 623/17.16 |
| 2015/0202051 A1 | 7/2015 | Tanaka et al. |
| 2016/0045334 A1 | 2/2016 | Ries |
| 2016/0081722 A1 | 3/2016 | Josse et al. |
| 2016/0166261 A1 | 6/2016 | Kleiner |
| 2016/0166402 A1 | 6/2016 | Steib |
| 2016/0184110 A1 | 6/2016 | Lambrecht et al. |
| 2017/0020579 A1 | 1/2017 | Aitarac et al. |
| 2017/0100260 A1 | 4/2017 | Duffield et al. |
| 2017/0224397 A1 | 8/2017 | Grimberg et al. |
| 2017/0238984 A1 | 8/2017 | Kleiner |
| 2017/0239067 A1 | 8/2017 | Nino |

OTHER PUBLICATIONS

Biomet. Solitaire Anterior Spinal System, [online], [retrieved on Sep. 29, 2014]. Retrieved from the Internet <URL:http://www.biomet.com/spine/products.cfm?pdid=3&majcid=14&prodid=220>.

DePuy Synthes. ACIS Anterior Cervical Interbody Spacer, [online], [retrieved on Sep. 29, 2014]. Retrieved from the Internet <URL:https://www.depuysynthes.com/hcp/spine/products/qs/ACIS-Anterior-Cervical-Interbody-Spacer>.

LDR Global Home. VerteBRIDGE Plating Technology, [online], [retrieved on Sep. 29, 2014], Retrieved from the Internet <URL:http://www.ldr.com/products/vertebridge>.

Stryker. Stryker AVS Anchor-C Cervical Cage System, [online], [retrieved on Sep. 29, 2014]. Retrieved from the Internet <URL:http://www.stryker.com/en-us/products/Spine/Cervical/Anchor-C/index.htm>.

* cited by examiner

SPINAL IMPLANT INSERTION TOOL

CROSS REFERENCE TO RELATED APPLICATIONS

This application is a continuation-in-part of U.S. patent application Ser. No. 15/958,629 filed on Apr. 20, 2018, which is hereby incorporated by reference in its entirety.

BACKGROUND

The present invention relates to tools for implanting spinal implants onto or into the spine of a patient.

Spinal implants, such as spinal plates or spinal cages, may be used to stabilize the spine, assist with fusion, or to strengthen the spine. At times, it may be desired to implant multiple spinal implants during the same operation. Some spinal implant insertion tools are only capable of holding one spinal implant at a time. In order to implant multiple spinal implants, the spinal implant tool must be removed from the body and reinserted into the body to implant a second or a third spinal implant. This creates a risk of injuring the patient upon removal or reinsertion. Therefore, it would be desirable for a spinal implant insertion tool to be capable of securing multiple spinal implants simultaneously so that the multiple spinal implants may be inserted without having to remove the spinal implant insertion tool.

Thus, there is a need for improvement in this field.

SUMMARY

The claims, and only the claims, recite the invention. In summary, it may include a spinal implant insertion tool for implanting at least two separate implants into or onto the spine of a patient.

The spinal implant insertion tool includes a handle portion and an attachment portion extending distally from the handle portion. A first attachment section is positioned on the attachment portion and adapted to secure a surgically sterile spinal plate to the spinal implant insertion tool. A second attachment section is positioned on the attachment portion distally of the first attachment section. The second attachment section is adapted to secure a surgically sterile spinal cage to the spinal implant insertion tool. The second attachment section is sized to allow the second attachment section to pass through an opening in the spinal plate before the spinal plate is secured to the first attachment section.

In some embodiments, a method of implanting at least two spinal implants using a spinal implant insertion tool includes passing a spinal plate over a second attachment section of the spinal implant insertion tool. The spinal plate is then attached to a first attachment section of a spinal implant insertion tool. The second attachment section is positioned distally of the first attachment section. A spinal cage is attached to the second attachment section of the spinal implant insertion tool.

The spinal implant insertion tool is operated by a user to position the spinal cage into the disc space between the vertebral bodies of a patient, and the spinal plate is secured to an anterior surface of the vertebral bodies. The spinal cage is then decoupled from the second attachment section of the spinal implant insertion tool and the spinal plate is decoupled from the first attachment section of the spinal implant insertion tool.

In some embodiments, the spinal implant insertion tool includes a handle portion formed by a proximal end of a first prong and a second prong and also includes an attachment portion formed by a distal end of the first prong and the second prong. A hinged portion is positioned between the handle portion and the attachment portion. The first prong and the second prong are coupled by a hinge in the hinged portion. A first attachment section of the attachment portion includes first connectors configured to hold a spinal plate. One of the first connectors is positioned on the first prong and another of the first connectors is positioned on the second prong. A second attachment section of the attachment portion includes second connectors configured to hold a spinal cage. One of the second connectors is positioned on the first prong and another of the second connectors is positioned on the second prong. The second attachment section is positioned distally of the first attachment section.

A hinge axis is defined through the second prong and the hinge. A spinal implant axis is defined through a center of the spinal plate and a center of the spinal cage when the spinal plate is held in the first attachment section and the spinal cage is held in the second attachment section. The hinge axis and the spinal implant axis are spaced from each other so that the hinge axis is offset from the spinal implant axis and the hinge axis and the spinal implant axis are not collinear.

Further forms, objects, features, aspects, benefits, advantages, and embodiments of the present invention will become apparent from a detailed description and drawings provided herewith.

DESCRIPTION OF THE SELECTED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

Figure 1:
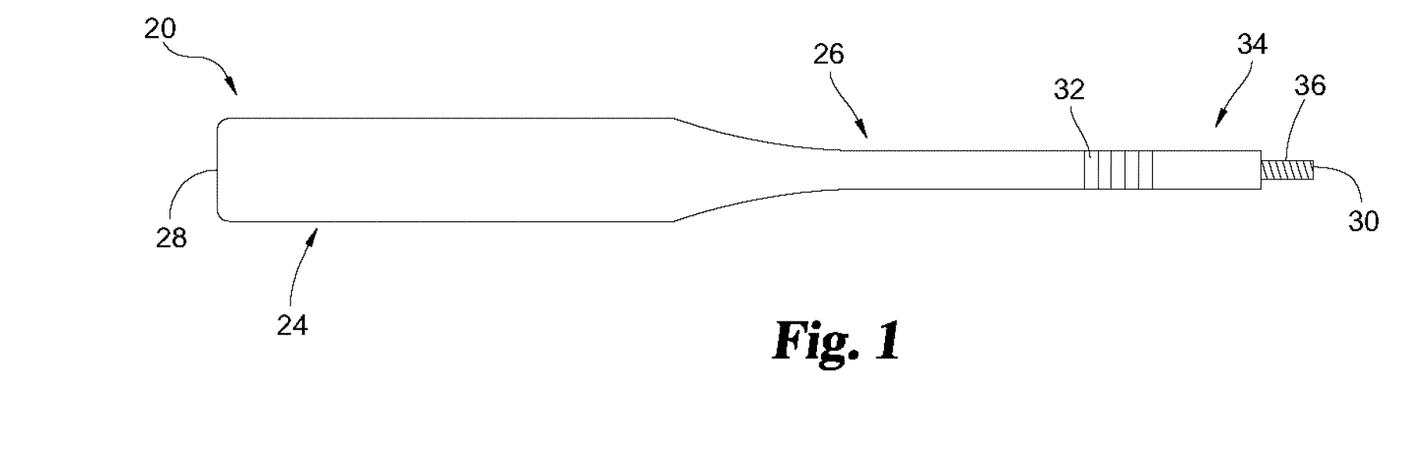
FIG. 1 is a side view of a spinal implant insertion tool.

With reference to the drawing Figures, for example FIGS. 1-8, a spinal implant insertion tool 20 is shown. The spinal implant insertion tool 20 may be used for implanting a single spinal implant or may be used for implanting two or more separate implants. As shown in FIG. 1, the spinal implant insertion tool 20 includes a handle portion 24 and an attachment portion 26 extending distally from the handle portion 24. The proximal end of the handle portion 24 includes a head 28, and the distal end of the attachment portion 26 includes a distal tip 30.

Figure 2:
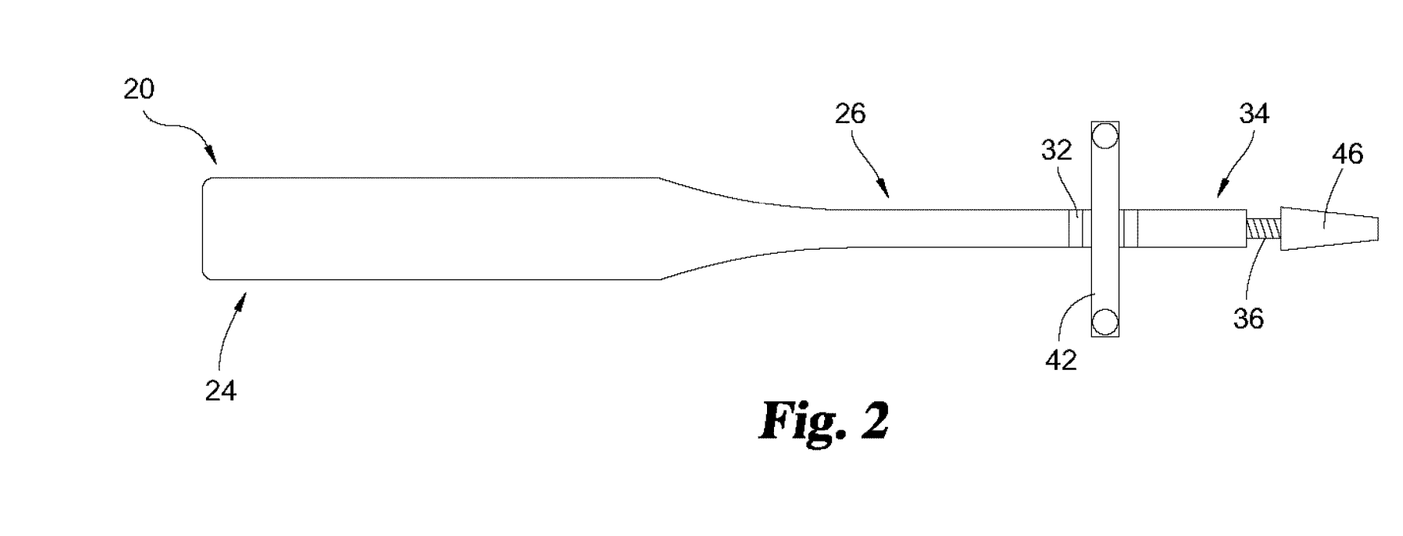
FIG. 2 is a side view of the spinal implant insertion tool of FIG. 1 with a spinal plate and a spinal cage attached to an attachment portion of the spinal implant insertion tool that includes threaded attachment sections.

A first attachment section 32 is positioned on the attachment portion 26 of the spinal implant insertion tool 20 and adapted to secure a surgically sterile spinal plate 42 to the spinal implant insertion tool 20 (see FIG. 2). In some embodiments, the spinal plate 42 is adapted to be attached to the anterior side of one or more vertebral bodies in a patient's spine.

A second attachment section 36 positioned on the attachment portion 26, so that the second attachment section 36 is distal of the first attachment section 32. The second attachment section 36 is adapted to secure a surgically sterile spinal cage 46 to the spinal implant insertion tool 20 (See FIG. 2). The second attachment section is sized to allow the second attachment section 36 to pass through an opening in the spinal plate before the spinal plate is secured to the first attachment section 32.

One feature that is optional, but not required, may be that the first attachment section 32 is adapted to be rotated with respect to the spinal plate 42 to attach the spinal plate 42 to the first attachment section 32. In some embodiments where rotation is used to attach the spinal plate 42 to the first attachment section 32, the first attachment section 32 is threaded and is coupled with a threaded opening in the spinal plate 42.

Figure 3:
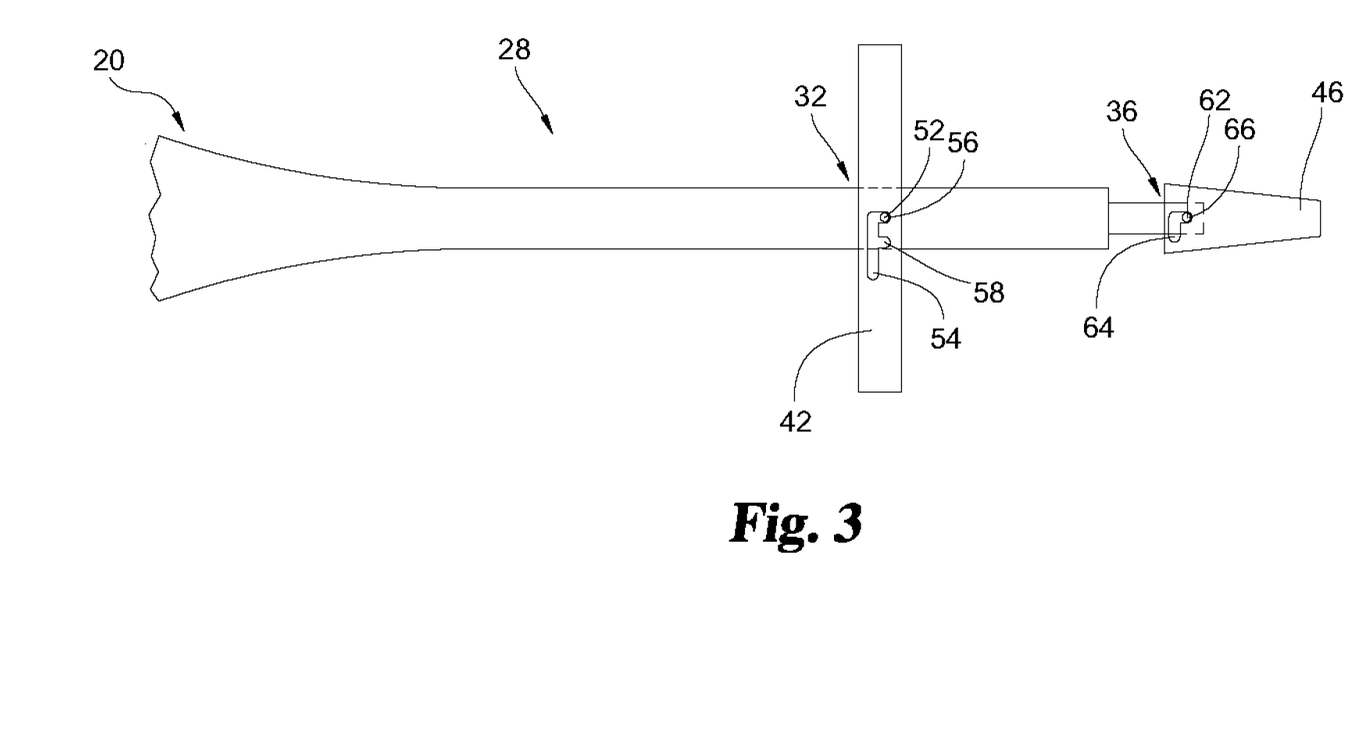
FIG. 3 is a side view of an embodiment of a spinal implant insertion tool with a spinal plate and a spinal cage attached to an attachment portion of the spinal implant insertion tool that includes bayonet mounts.

In another embodiment, the first attachment section 32 is adapted to attach the spinal plate 42 using a bayonet mount. The bayonet mount includes a pin 52 and a corresponding slot 54. As shown in FIG. 3, in some embodiments, the pin 52 may be located on the spinal implant insertion tool 20 while the slot 54 is defined in the spinal plate 42. However, in other embodiments the pin 52 may be located on the spinal plate 42 while the slot 54 is defined in the spinal implant insertion tool 20.

One feature that is optional, but not required, may be that the second attachment section 36 is adapted to be rotated with respect to the spinal cage 46 to attach the spinal cage 46 to the second attachment section 36. In some embodiments where rotation is used to attach the spinal cage 46 to the second attachment section 36, the second attachment section 36 is threaded and is coupled with a threaded opening in the spinal cage 46.

In another embodiment, the second attachment section 36 is adapted to attach the spinal cage 46 using a bayonet mount. The bayonet mount includes a pin 62 and a corresponding slot 64. As shown in FIG. 3, in some embodiments, the pin 62 may be located on the spinal implant insertion tool 20 while the slot 64 is defined in the spinal cage 46. However, in other embodiments the pin 62 may be located on the spinal cage 46 while the slot 64 is defined in the spinal implant insertion tool 20.

In some embodiments, the first attachment section 32 and the second attachment section 36 are both threaded. In other embodiments, the first attachment section 32 and the second attachment section 36 are both bayonet mounts. In still other embodiments, spinal implant insertion tool 20 includes any desired mixture of different types of attachment sections. For example, first attachment section 32 is threaded while second attachment section 36 is a bayonet mount.

One feature that is optional, but not required, may be that the first attachment section 32 and/or the second attachment section 36 may include an expansion point where the diameter or the width of attachment portion is increased. The spinal plate 42 may attach to the first attachment section 32 at the expansion point by a friction fit. Likewise, the spinal cage 46 may attach to the second attachment section 36 at the expansion point by a friction fit.

One feature that is optional, but not required, may be that the second attachment section 36 is positioned at the distal tip 30 of the attachment portion 26. Another optional feature is that a gap 34 is defined on the attachment portion 26 between the first attachment section 32 and the second attachment section 36, so that there is a separation between the spinal plate 42 and the spinal cage 46 when the spinal plate 42 and spinal cage 46 are attached to respective attachment sections 32, 36.

One feature that is optional, but not required, may be that the width of the second attachment section 36 is equal to or smaller than the width of the first attachment section 32.

One feature that is optional, but not required, may be that the spinal plate 42 is adapted to be attached to the anterior side of one or more vertebral bodies in a patient's spine. The spinal cage 46 is adapted to be inserted between two vertebral bodies 70, 80 of a patient's spine. In some embodiments, the spinal cage 46 is inserted between the two vertebral bodies by applying force to the head 28 of the handle portion 24 with a hammer. In other embodiments, the spinal cage 46 is inserted between the two vertebral bodies by rotating the handle portion 24 so that the spinal cage 46 is threaded between the two vertebral bodies.

A method for inserting a spinal implant between two vertebral bodies includes passing the spinal plate 42 over the second attachment section 36 of the spinal implant insertion tool 20. The spinal plate 42 is then attached to the first attachment section 32 of the spinal implant insertion tool 20. After attaching the spinal plate 42, the spinal cage 46 is attached to the second attachment section 36 of the spinal implant insertion tool 20.

Figure 4:
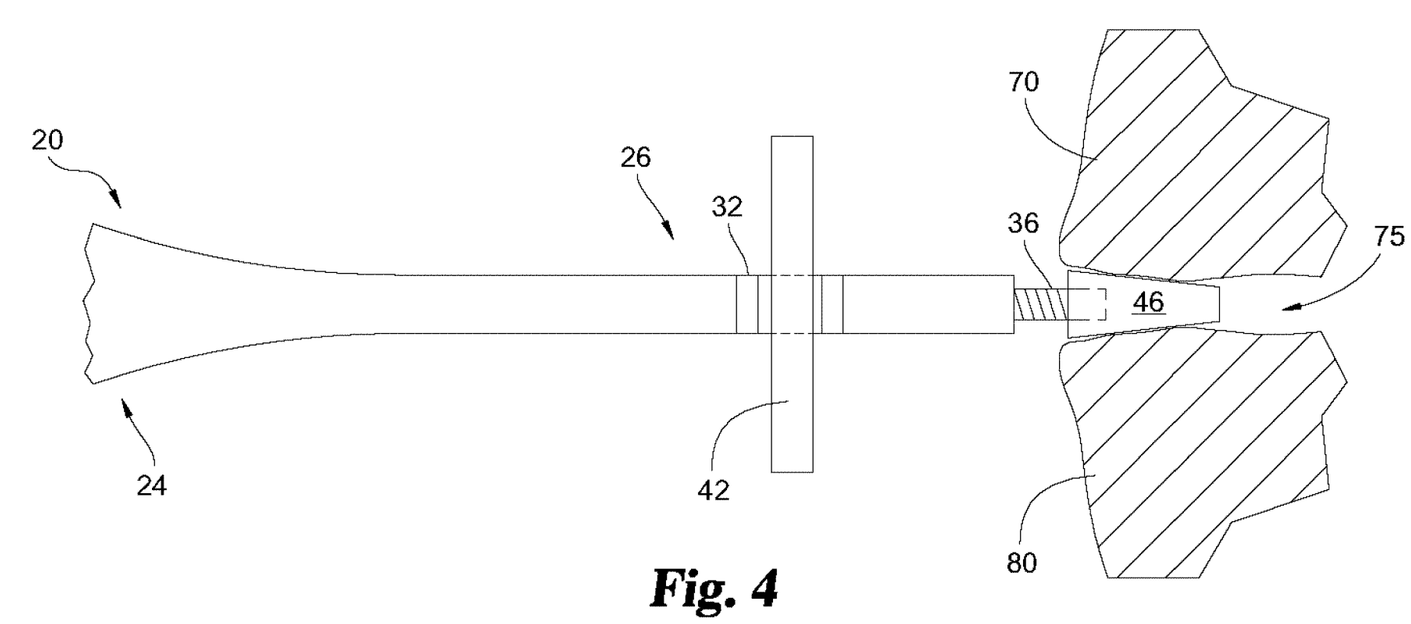
FIG. 4 is a side view of a spinal cage and spinal plate being implanted using the spinal implant insertion tool of FIG. 1.
Figure 5:
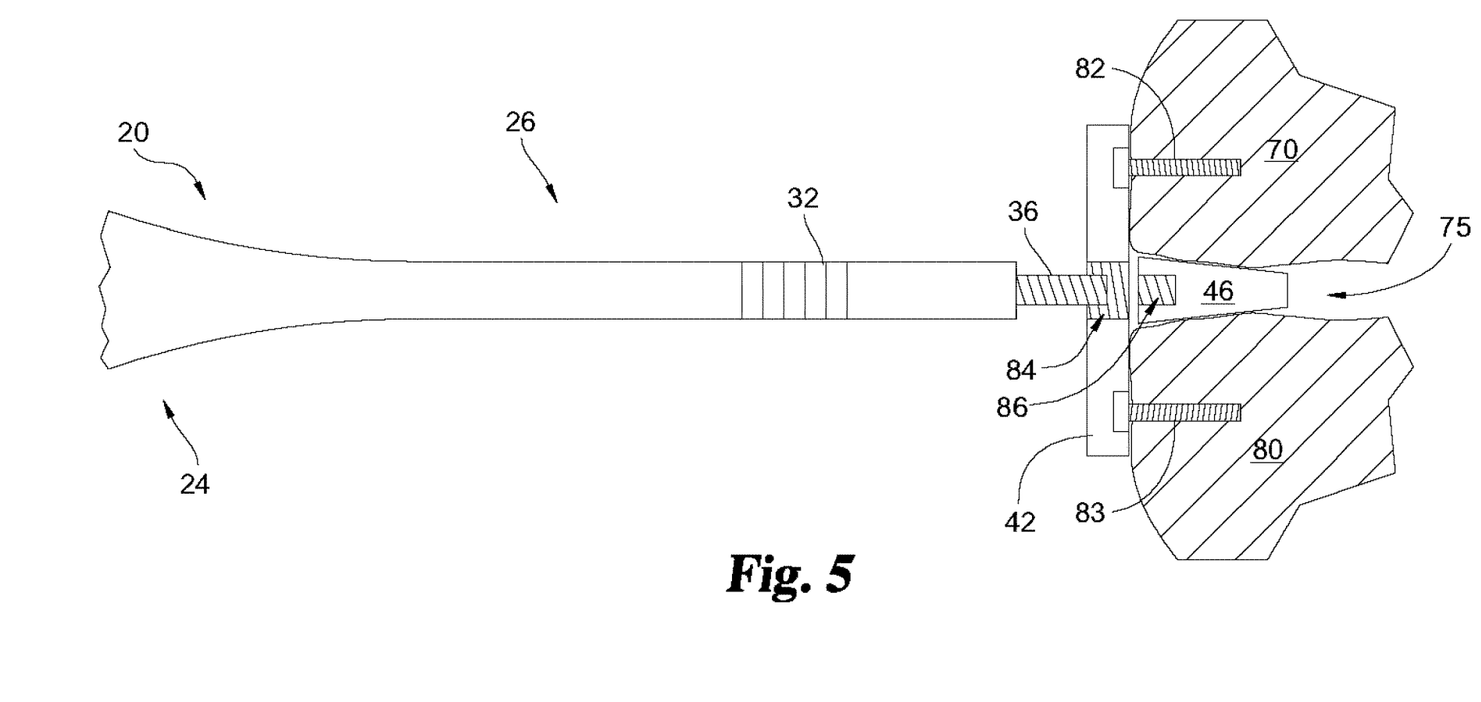
FIG. 5 is a cross-sectional side view of the spinal implant insertion tool of FIG. 1 being decoupled from the spinal plate and spinal cage after implantation.

As shown in FIG. 4, after attaching to the spinal implant insertion tool 20, the spinal cage 46 is positioned into the disc space 75 between two vertebral bodies 70, 80. The spinal plate 42 is secured to an anterior surface of the vertebral bodies 70, 80. As an example, the spinal plate 42 may be secured using screws 82, 83 that extend into the anterior surface of a respective vertebral body 70 or 80. In other embodiments, the spinal plate 42 may be secured to the vertebral bodies 70, 80 using screws or rods extending through the end plates of the vertebral bodies 70, 80 or through both the anterior surface and the endplates of vertebral bodies 70, 80.

The spinal cage 46 is then decoupled from the second attachment section 36 of the spinal implant insertion tool 20, and the spinal plate 42 is decoupled from the first attachment section 32. It should be recognized that the order of securing the spinal plate 42 to the vertebral bodies and decoupling the spinal cage 46 and the spinal plate 42 from the insertion tool may vary in different embodiments. As an example, in one embodiment, the spinal cage 46 is decoupled from the second attachment section 36, then the spinal plate 42 is attached to the vertebral bodies 70, 80 and then the spinal plate 42 is decoupled from the first attachment section 32. In another embodiment, the spinal plate 42 is attached to the vertebral bodies 70, 80 and then the spinal plate 42 and the spinal cage 46 are decoupled from the respective attachment sections 32 and 36 simultaneously.

One feature that is optional, but not required, may be that the spinal plate 42 is attached to the first attachment section 32 by rotating the first attachment section 32 with respect to the spinal plate 42. In some embodiments, the first attachment section 32 is threaded and corresponds to a threaded opening 84 defined in the spinal plate 42 (see FIG. 5). Attaching the spinal plate 42 to the first attachment section 32 includes threading the first attachment section 32 through the threaded opening 84 in the spinal plate 42. In other embodiments, the spinal plate 42 is coupled to the first attachment section 32 using a bayonet mount.

Another feature that is optional, but not required, may be that the spinal cage 46 is attached to the second attachment section 36 by rotating the second attachment section 36 with respect to the spinal cage 46. In some embodiments, the second attachment section 36 is threaded, and a threaded opening 86 is defined in the spinal cage 46 (see FIG. 5). Attaching the spinal cage 46 to the second attachment section 36 includes threading the second attachment section 36 through the threaded opening 86 in the spinal cage 46. In other embodiments, the spinal cage 46 is coupled to the second attachment section 36 using a bayonet mount.

One feature that is optional, but not required, may be that decoupling the spinal plate 42 from the first attachment section 32 includes unthreading the first attachment section 32 from the threaded opening 84 defined in the spinal plate 42. Similarly, another feature that is optional, but not required, may be that decoupling the spinal cage 46 from the second attachment section 36 includes unthreading the second attachment section 36 from the threaded opening 86 defined in the spinal cage 46.

One feature that is optional, but not required, may be that decoupling the spinal cage 46 from the second attachment section 36 of the spinal implant insertion tool 20 includes rotating the spinal implant insertion tool 20 by a first amount of rotation. Then, decoupling the spinal plate 42 from the first attachment section 32 of the spinal implant insertion tool 20 includes rotating the spinal implant insertion tool 20 by a second amount of rotation. The second amount of rotation required to decouple the spinal plate 42 is greater than the first amount of rotation required to decouple the spinal cage 46. In other embodiments, the second amount of rotation required to decouple the spinal plate 42 is less than the first amount of rotation required to decouple the spinal cage 46.

As an example, in FIG. 3, the first attachment section 32 and the second attachment section 36 both include a bayonet mount. The slot 54 in the spinal plate 42 includes two detents 56, 58 and the slot 64 in the spinal cage 46 includes a single detent 66. After the spinal implant insertion tool 20 is rotated to remove the spinal cage 46, the pin 52 at the first attachment section 32 may be inserted into the detent 58 to keep the spinal plate 42 attached to the first attachment section 32. The spinal implant insertion tool 20 may be rotated again to remove the spinal plate 42 from the first attachment section 32.

One feature that is optional, but not required, may be that positioning the spinal cage 46 into the disc space 75 between the vertebral bodies 70, 80 includes hammering the head 28 that is integral with or coupled to the handle portion 24 to force the spinal cage 46 between the vertebral bodies 70, 80. In other embodiments, positioning the spinal cage 46 between the vertebral bodies 70, 80 includes rotating the handle portion 24 to thread the spinal cage 46 between the vertebral bodies 70, 80.

One feature that is optional, but not required, may be that decoupling the spinal cage 46 from the second attachment section 36 is completed before decoupling the spinal plate 42 from the first attachment section 32. In other embodiments, decoupling the spinal plate 42 from the first attachment section 32 is completed before decoupling the spinal cage 46 from the second attachment section 36. In still other embodiments, decoupling the spinal plate 42 from the first attachment section 32 and decoupling the spinal cage 46 from the second attachment section 36 are performed simultaneously.

Figure 6:
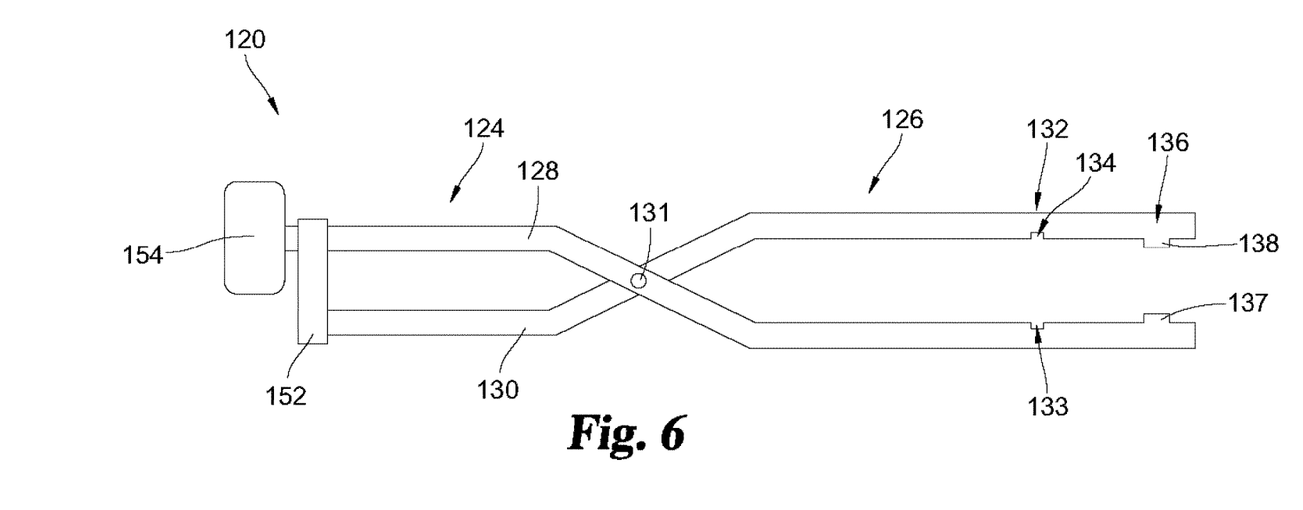
FIG. 6 is a side view of an embodiment of a spinal implant insertion tool in a closed position.
Figure 7:
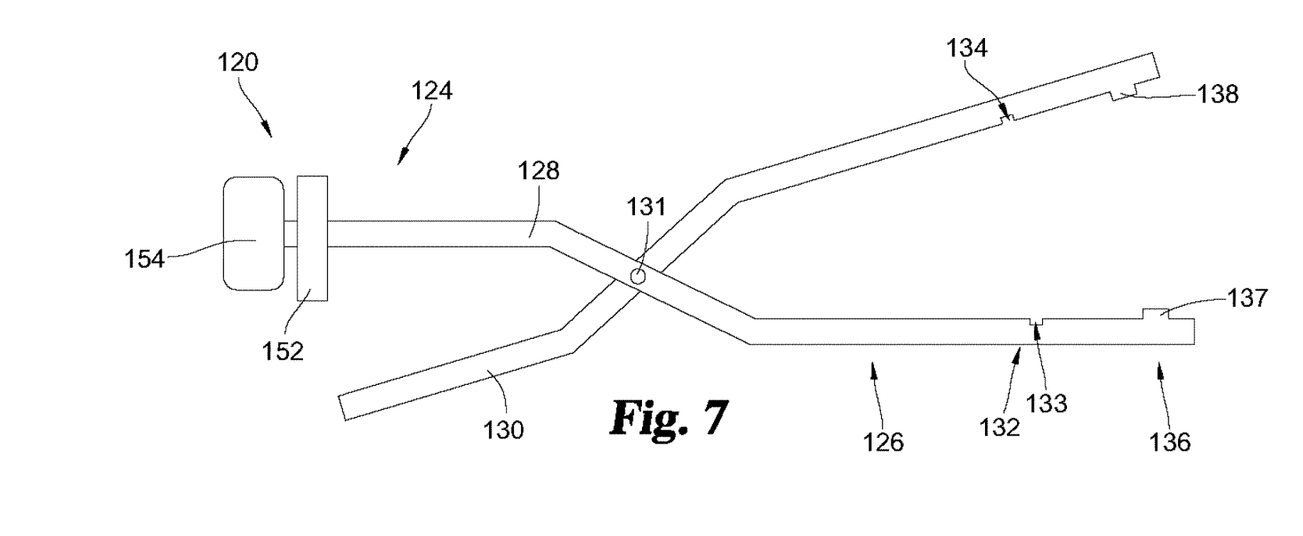
FIG. 7 is a side view of the spinal implant insertion tool of FIG. 6 in an open position.
Figure 8:
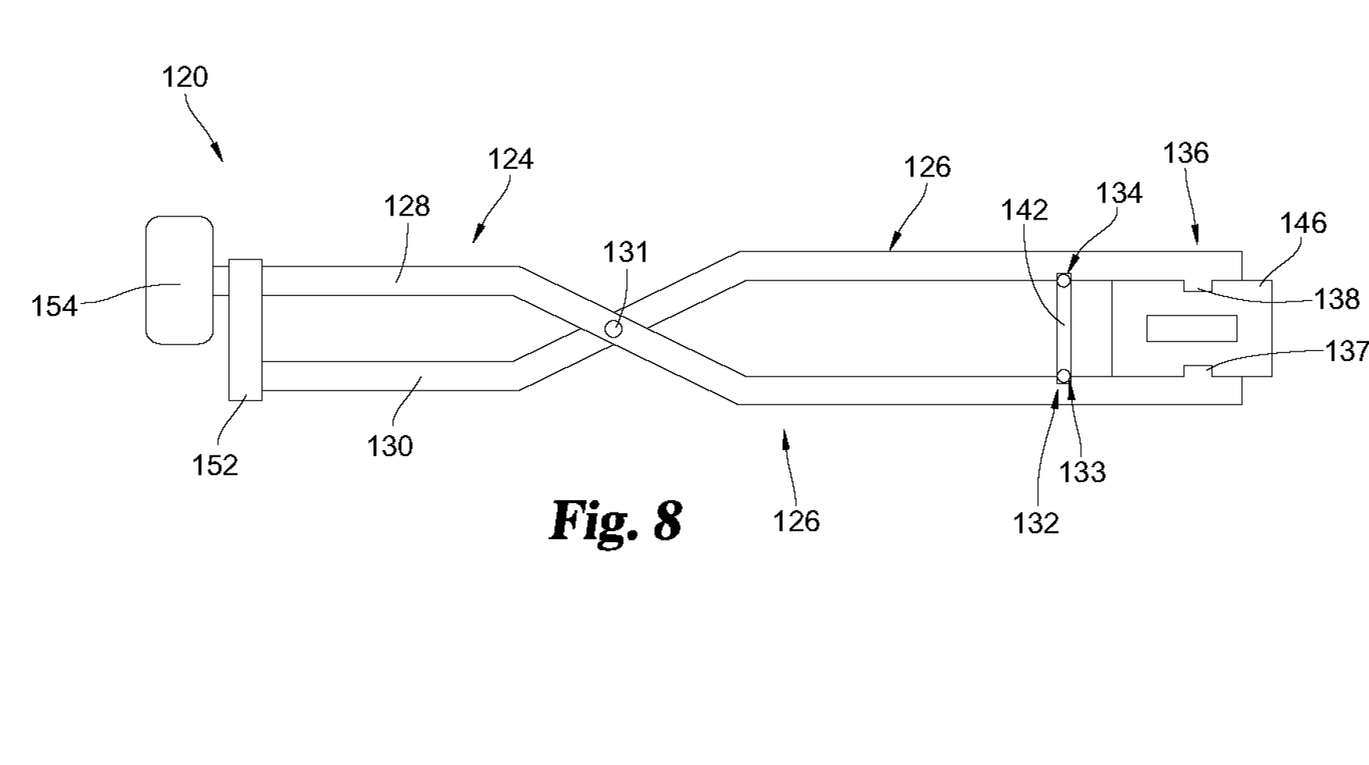
FIG. 8 is a side view of the spinal implant insertion tool of FIG. 6 holding a spinal plate and a spinal cage.

An alternative embodiment of a spinal implant insertion tool 120 is shown in FIGS. 6-8. The spinal implant insertion tool includes a handle portion 124 formed by a proximal end of a first prong 128 and a second prong 130 coupled at a hinge 131. An attachment portion 126 of the spinal implant insertion tool 120 is formed by a distal end of the first prong 128 and the second prong 130.

A first attachment section 132 of the attachment portion 126 includes first connectors 133, 134 configured to hold a spinal plate 142 (see FIG. 8). One of the first connectors 133 is positioned on the first prong 128 and another of the first connectors 134 is positioned on the second prong 130.

A second attachment section 136 of the attachment portion 126 includes second connectors 137, 138 configured to hold a spinal cage 146 (see FIG. 8). One of the second connectors 137 is positioned on the first prong 128 and another of the second connectors 138 is positioned on the second prong 130. The second attachment section 136 is positioned distally of the first attachment section 132.

One feature that is optional, but not required, may be that each of the first connectors 133, 134 is a divot defined in a respective first prong 128 or second prong 130. Another optional feature may be that each of the second connectors 137, 138 is a protrusion extending from a respective first prong 128 or second prong 130.

One feature that is optional, but not required, may be a locking collar 152 attached to or integral with the handle portion 124. As shown in FIGS. 6 and 8, the locking collar 152 is configured to prevent the prongs 128, 130 from moving about the hinge 131 when the locking collar 152 engages both the first prong 128 and the second prong 130.

One feature that is optional, but not required, may be a head 154 attached to or integral with one of the prongs 128, 130 of the handle portion 124. In some embodiments, the head 154 has a greater width than the width of the first prong 128 or the second prong 130, allowing the head 154 to better withstand force from a hammer without breaking. In FIGS. 6-8, head 154 is shown to be at the proximal end of handle portion 124; however, in other embodiments, head 154 may be positioned at other locations on the spinal implant insertion tool 120.

Another alternative embodiment of a spinal implant insertion tool 220 is shown in FIGS. 9-13. The spinal implant insertion tool includes a handle portion 224 formed by a proximal end of a first prong 228 and a second prong 230 coupled at a hinge 231. An attachment portion 226 of the spinal implant insertion tool 220 is formed by a distal end of the first prong 228 and the second prong 230.

The first prong 228 is nonlinear. The handle portion 224 of the first prong 228 is parallel to the attachment portion 226 portion of the first prong 228. A hinged portion 225 of the first prong 228 is positioned between the handle portion 224 of the first prong 228 and the attachment portion 226 of the first prong 228. The hinge 231 that attaches the first prong 228 to the second prong 230 is positioned at the hinged portion 225. The hinged portion 225 of first prong 228 extends at an oblique angle with respect to the handle portion 224 of the first prong 228 and the attachment portion 226 of the first prong 228. The second prong 230 is linear and does not include an oblique angle.

Figure 11:
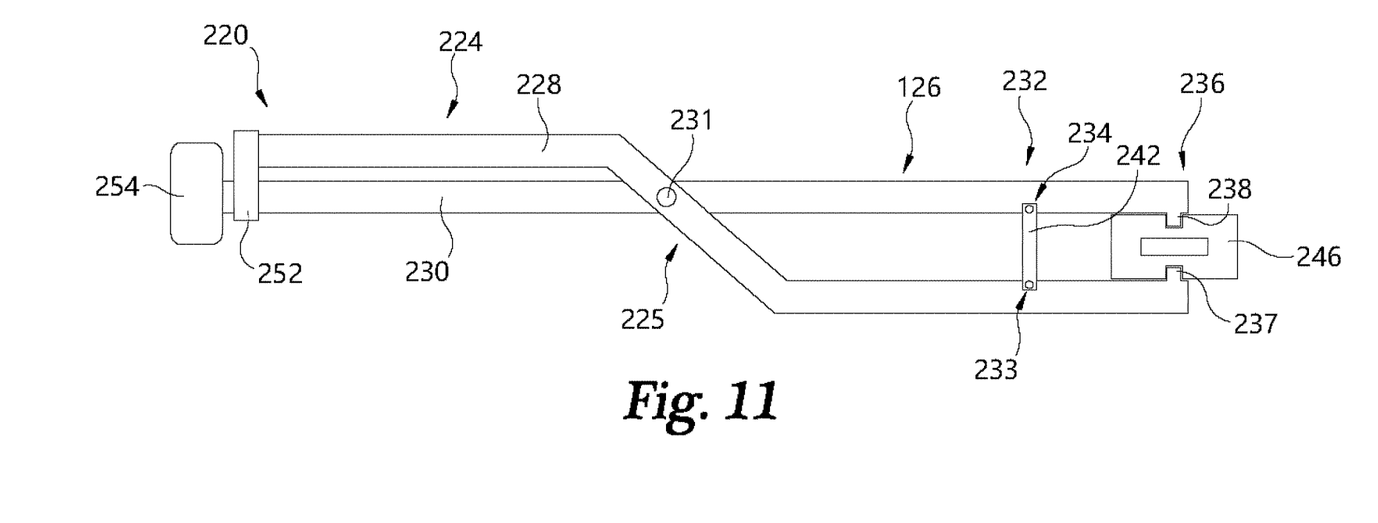
FIG. 11 is a side view of the spinal implant insertion tool of FIG. 9 holding a spinal plate and a spinal cage.

A first attachment section 232 of the attachment portion 226 includes first connectors 233, 234 configured to hold a spinal plate 242 (see FIG. 11). One of the first connectors 233 is positioned on the first prong 228 and another of the first connectors 234 is positioned on the second prong 230. A second attachment section 236 of the attachment portion 226 includes second connectors 237, 238 configured to hold a spinal cage 246 (see FIG. 11). One of the second connectors 237 is positioned on the first prong 228 and another of the second connectors 238 is positioned on the second prong 230. The second attachment section 236 is positioned distally of the first attachment section 232. As shown, the first attachment section 232 is capable of holding the spinal plate 242 simultaneously as the second attachment section is holding the spinal cage 246.

Figure 12:
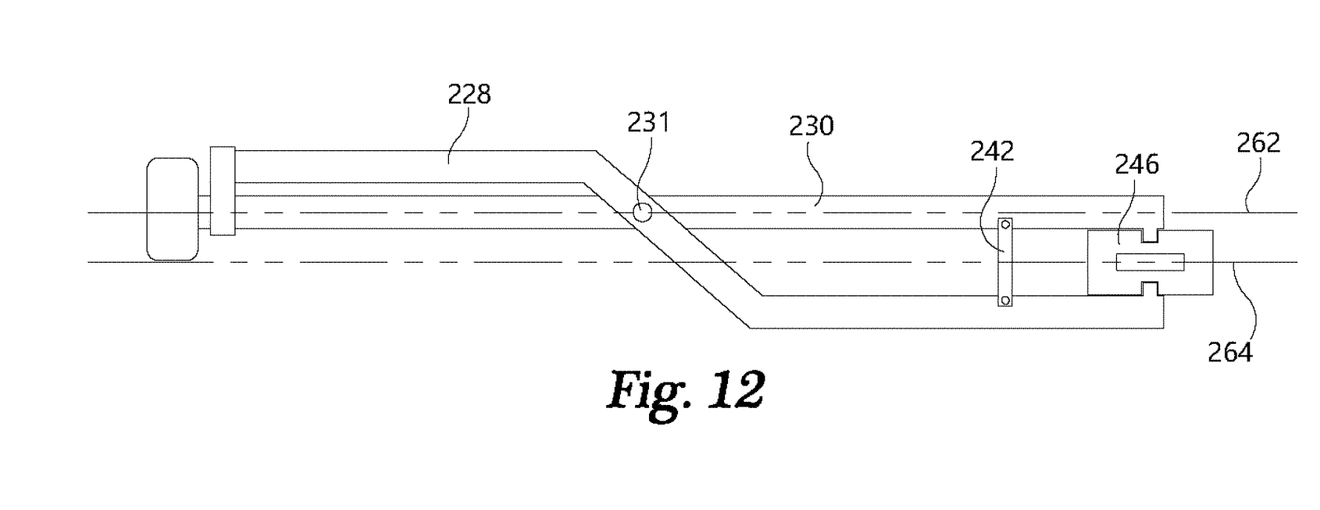
FIG. 12 is a side view of a hinge axis and a spinal implant axis of the spinal implant insertion tool of FIG. 9.

As illustrated in FIG. 12, because the second prong 230 is linear and does not include an oblique portion similar to first prong 228, the hinge 231 is offset from the spinal plate 242 and the spinal cage 246. A hinge axis 262 extends through the hinge 231 and through the second prong 230. A spinal implant axis 264 extends through the center of the spinal plate 242 and the spinal cage 246 when the spinal plate 242 and the spinal cage 246 are held in the first attachment section 232 and the second attachment section 236, respectively. Because the hinge 231 is offset, the hinge axis 262 is spaced from the spinal implant axis 264 so that the hinge axis 262 and the spinal implant axis 264 are not collinear. This offset configuration allows screws to be more easily placed through the spinal plate 242 and the spinal cage 246 while the spinal implant insertion tool 220 is holding both the spinal plate 242 and the spinal cage 246 because the hinge 231 does not get in the way of a tool inserting the screws.

One feature that is optional, but not required, may be that each of the first connectors 233, 234 is a divot defined in a respective first prong 228 or second prong 230. Another optional feature may be that each of the second connectors 237, 238 is a protrusion extending from a respective first prong 228 or second prong 230.

Figure 9:
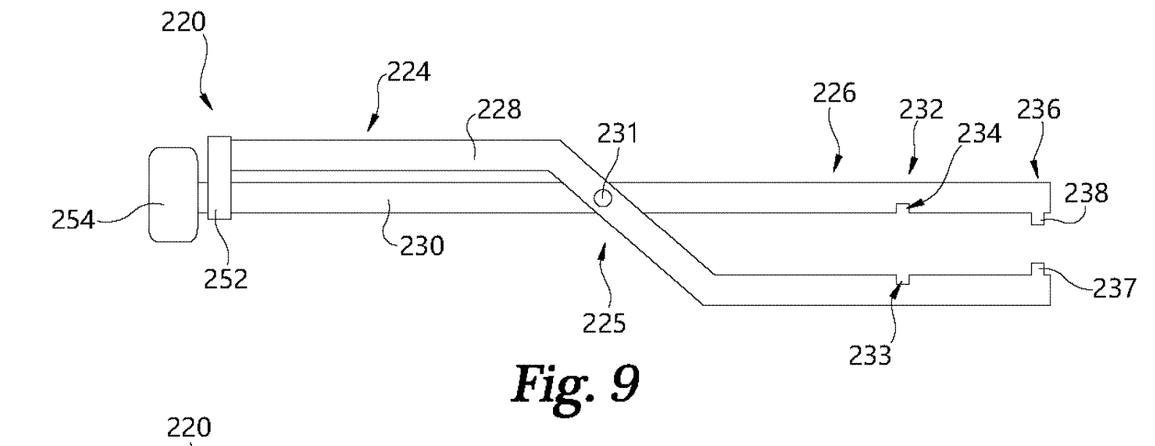
FIG. 9 is a side view of an embodiment of a spinal implant insertion tool in a closed position.
Figure 10:
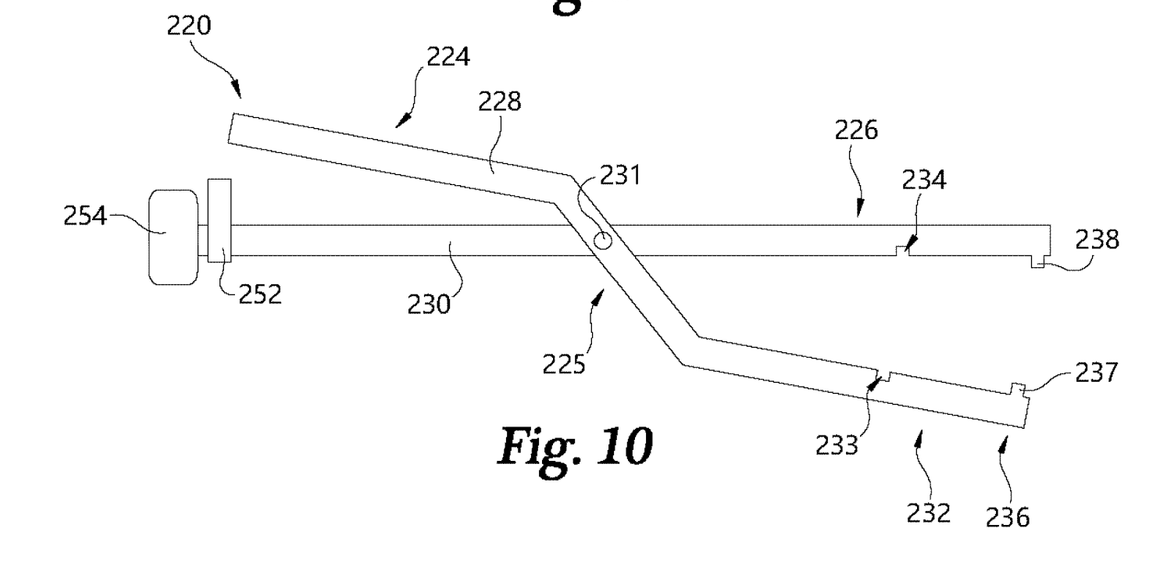
FIG. 10 is a side view of the spinal implant insertion tool of FIG. 9 in an open position.

One feature that is optional, but not required, may be a locking collar 252 attached to or integral with the handle portion 224. As shown in FIGS. 9 and 11, the locking collar 252 is configured to prevent the prongs 228, 230 from moving about the hinge 231 when the locking collar 252 engages both the first prong 228 and the second prong 230.

One feature that is optional, but not required, may be a head 254 attached to or integral with one of the prongs 228, 230 of the handle portion 224. In some embodiments, the head 254 has a greater width than the width of the first prong 228 or the second prong 230, allowing the head 254 to better withstand force from a hammer without breaking. In FIGS. 9-12, head 254 is shown to be at the proximal end of handle portion 224; however, in other embodiments, head 254 may be positioned at other locations on the spinal implant insertion tool 220.

Figure 13:
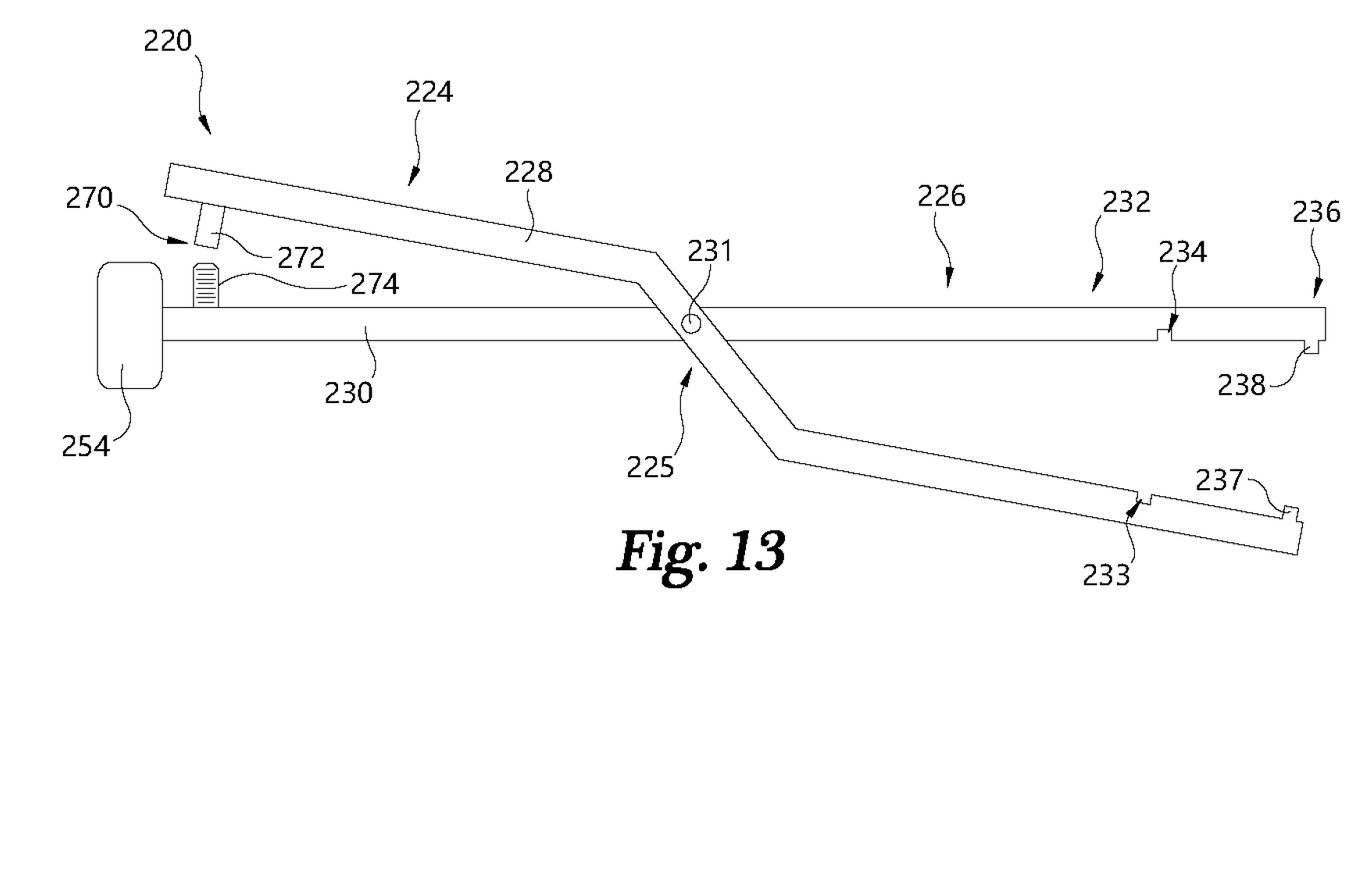
FIG. 13 is a side view of an embodiment of a spinal implant insertion tool that includes a serrated closure mechanism.

One feature that is optional, but not required, may be a serrated ratchet closure 270 (see FIG. 13). The serrated ratchet closure 270 includes a first latch 272 positioned on the handle portion 224 of the first prong 228 and a second latch 274 on the handle portion 224 of the second prong 230. The first and second latches 272, 274 may be brought in contact with each other to interlock to prevent the prongs 228, 230 from moving about the hinge 231. The first and second latches 272, 274 may also be pulled about from each other so that they are no longer in contact to allow the prongs 228, 230 to move about hinge 231.

As shown in FIG. 13, in some embodiments, the first latch 272 and the second latch 274 may each include serrations to allow for the spinal implant insertion tool 220 to be held open at an adjustable position. However, in other embodiments, only the first latch 272 is serrated and the second latch 274 includes another suitable method of connecting and interlocking with the first latch 272, such as an opening or a single hook. In still other embodiments, the second latch 274 may be serrated while the first latch 272 includes an alternative method of interlocking with the second latch 274.

One feature that is optional, but not required, is that the spinal implant insertion tool is unlocked by any suitable method that simultaneously disengages both the spinal plate 242 and the spinal cage 246 at the same time. This method could be the serrated ratchet closure as described above, or may be another method which allows simultaneous release of both the spinal plate 242 and the spinal cage 246.

As used here (claims, specification, and other definitions) the following terms have the following meaning:

Articles and phrases such as, "the", "a", "an", "at least one", and "a first", "comprising", "having" and "including" here are not limited to mean only one, but rather are inclusive and open ended to also include, optionally, two or more of such elements and/or other elements. In terms of the meaning of words or terms or phrases herein, literal differences therein are not superfluous and have different meaning, and are not to be synonymous with words or terms or phrases in the same or other claims.

The term "means for" in a claim invokes 35 U.S.C. § 112(f), literally encompassing the recited function and corresponding structure and equivalents thereto. Its absence does not, unless there otherwise is insufficient structure recited for that claim element. Nothing herein or elsewhere restricts the doctrine of equivalents available to the patentee.

The term "and/or" is inclusive here, meaning "and" as well as "or". For example, "P and/or Q" encompasses, P, Q, and P with Q; and, such "P and/or Q" may include other elements as well.

The term "anterior" as used herein has the meaning: being situated nearest or toward the front of the body. With respect to the spine, the anterior is considered to be the side of the spine closest to the stomach or the throat.

The term "attachment portion" as used herein has the meaning: an area or portion of the spinal implant tool that is designed to be capable of holding, securing, coupling, and/or attaching a spinal implant or multiple spinal implants to the tool to provide stability for the spinal implant during insertion. The attachment portion may include a single attachment section designed to hold a single spinal implant or may have multiple attachment sections, so that multiple spinal implants can be held by the attachment portion.

The term "attachment section" as used herein has the meaning: a part of the attachment portion of the spinal implant tool at which a spinal implant is held, secured, coupled, and/or attached to the spinal implant tool. The attachment section can include any feature that allows attachment of a spinal implant. For example, the attachment section may include threading, features for a bayonet mount, increased diameter to create a friction fit with a spinal implant, or any other suitable attachment mechanism.

The term "bayonet mount" as used herein has the meaning: any type of fastener that includes a male connector that includes a radial pin and a female connector that includes an opening and a slot for receiving the male connector. The radial pin is capable of sliding within the slot and is biased by a spring or any other suitable biasing force to keep the male connector and female connector locked together.

The term "collinear" as used herein has the meaning: overlapping or lying on the same straight line.

The term "connector" as used herein has the meaning: a portion of a prong that is used to hold, secure, couple, and/or attach a spinal implant to the prong. A connector may be a divot, a protrusion, or any other suitable feature or device on a prong that provides an improved connection with a spinal implant.

The term "distal" as used herein has the meaning: in a direction situated farther away from a given reference point. With respect to the spinal implant tool, the distal direction is in the direction away from the handle portion and toward the attachment portion.

The term "distal tip" as used herein has the meaning: the portion of the spinal implant tool that includes the distal-most limit of the spinal implant tool. The distal tip may include the distal-most limit of the spinal implant tool and the portion the of the spinal implant tool immediately adjacent to the distal-most limit.

The term "divot" as used herein has the meaning: a depression, recess, or concavity in a surface.

The term "gap" as used herein has the meaning: a break or an interval between two objects or two features of an object.

The term "hammer" as used herein has the meaning: any device used to assist with implantation of a spinal implant by applying an axial force to the spinal implant tool.

The term "handle portion" as used herein has the meaning: any part of a spinal implant tool that is designed to be held or gripped by a user while the spinal implant tool is used to install a spinal implant at a desired location on the spine.

The term "head" as used herein has the meaning: a portion of the handle portion of the spinal implant tool that is designed to withstand force applied by a hammer. The head may be the proximal end of the handle portion or may be a different part of the handle portion that is designed to be struck by a hammer. The head may be a uniform part of the handle portion or may have a greater width or greater thickness than the rest of the handle portion to improve the ability of the head to withstand force applied by the hammer without breaking.

The term "hinge" as used herein has the meaning: a movable joint connecting linked objects that allows rotation of the linked objects with respect to each other.

The term "linear" as used herein has the meaning: arranged in or extending along a straight or nearly straight line. A feature that is linear lies along a single axis.

The term "locking collar" as used herein has the meaning: any device on a spinal implant tool that is capable of preventing the prongs of the spinal implant tool from rotating at the hinge. The locking collar may be integral to the spinal implant tool or may be a separate piece that is attached to or connects to the spinal implant tool.

The term "offset" as used herein has the meaning: out of line or not collinear.

The term "prong" as used herein has the meaning: any portion of a spinal implant tool that is attached at a hinge so that the prong may pivot or rotate with respect to other portions of the spinal implant tool.

The term "protrusion" as used herein has the meaning: any extension from a portion of a surface. A protrusion may be a convex portion of a surface or may be a separate piece that is attached to a given surface.

The term "proximal" as used herein has the meaning: in a direction situated closer to a given reference point. With respect to the spinal implant tool, the proximal direction is in the direction toward the handle portion and away from the attachment portion.

The term "serration" as used herein has the meaning: a tooth or a point of a notched or saw-like surface and/or edge. A serrated surface or edge may have a single serration or may include two or more serrations.

The term "simultaneously" as used herein has the meaning: occurring at the same time or at substantially the same time.

The term "spinal cage" as used herein has the meaning: a prosthetic device that is inserted into the disc space between two vertebral bodies. A spinal cage may be any desired shape that is capable of fitting between the vertebral bodies, such as cylindrical, rectangular, or square. A spinal cage may be threaded or may include teeth for attaching to the end plates of adjacent vertebrae. The spinal cage may be formed from metal, such as titanium, or may be made of other materials of suitable strength, such as a composite material like carbon fiber.

The term "spinal implant" as used herein has the meaning: a device attached to or positioned on the spine by a medical procedure. A spinal implant may be used to stabilize or strengthen the spine, or may be used to correct a deformity. Some examples of spinal implants may include, but are not limited to, rods, pedicle screws, hooks, plates, or cages.

The term "spinal plate" as used herein has the meaning: a device that is attached to the anterior or posterior of the spine to keep a portion of the spine from moving. A spinal plate may be attached to the spine using screws, rods, teeth, or any other suitable method. A spinal plate can span any number of desired vertebrae and may be made from metal, such as titanium, or any other suitable material.

The term "surgically sterile" as used herein has the meaning: free from harmful bacteria or any other microorganisms so as to be capable of being inserted or implanted either partially or completely within the body without causing a risk of sickness or infection.

The term "threaded" as used herein has the meaning: any object or portion of an object that includes screw threads for coupling with an opening that includes complimentary threads.

The term "threaded opening" as used herein has the meaning: an aperture or void that includes screw threads around the diameter for receiving and coupling with an object that includes complimentary threads.

The term "vertebral body" as used herein has the meaning: the largest, cylindrical part of a vertebra. The vertebra is a bone or object that forms part of the spinal column. The vertebral body could be composed of bone or it can be an implant formed from any variety of materials that would be useful to replace bone, such as titanium, stainless steel, or other metallic or non-metallic compounds.

The invention may include any one or more articles or devices made by any of the claimed methods and/or may by different methods but with a claimed composition.

The language used in the claims and the written description and in the above definitions is to only have its plain and ordinary meaning, except for terms explicitly defined above. Such plain and ordinary meaning is defined here as inclusive of all consistent dictionary definitions from the most recently published (on the filing date of this document) general purpose Webster's dictionaries and Random House dictionaries. While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A spinal implant insertion tool comprising:
   a handle portion formed by a proximal end of a first prong and a proximal end of a second prong;
   an attachment portion formed by a distal end of said first prong and a distal end of said second prong;
   a hinged portion positioned between said handle portion and said attachment portion, wherein said first prong and said second prong are coupled by a hinge in said hinged portion;
   a first attachment section of said attachment portion including first connectors configured to hold a spinal plate, wherein one of said first connectors is positioned on said first prong and another of said first connectors is positioned on said second prong; and
   a second attachment section of said attachment portion including second connectors configured to hold a spinal cage, wherein one of said second connectors is positioned on said first prong and another of said second connectors is positioned on said second prong;
   wherein said first prong is not continuously linear between its proximal and distal ends, and wherein said second prong is linear between its proximal and distal ends.

2. The spinal implant insertion tool of claim 1, wherein in the hinged portion, said first prong extends at an oblique angle with respect to the proximal end of said first prong and the distal end of said first prong.

3. The spinal implant insertion tool of claim 1, wherein the proximal end of said first prong is parallel to the distal end of said first prong.

4. The spinal implant insertion tool of claim 1, further comprising:
   a hinge axis that extends along said second prong and through said hinge;
   a spinal implant axis that extends through a center of the spinal plate and a center of the spinal cage when the spinal plate is held in said first attachment section and the spinal cage is held in said second attachment section; and
   wherein said hinge axis and said spinal implant axis are spaced from each other so that said hinge axis is offset from said spinal implant axis.

5. The spinal implant insertion tool of claim 1, further comprising:
   a locking collar attached to said handle portion, wherein said locking collar is configured to prevent said first prong and said second prong from moving about said hinge when said locking collar engages both said first prong and said second prong.

6. The spinal implant insertion tool of claim 1, further comprising:
   a head attached to said first prong at an end of said handle portion, wherein said head has a greater width than a width of said first prong.

7. The spinal implant insertion tool of claim 1, further comprising:
   a serrated ratchet closure positioned on said handle portion, wherein said serrated ratchet closure includes a first latch attached to said first prong and a second latch attached to said second prong; and
   wherein said first latch and said second latch are configured to interlock when in contact to prevent said first prong and said second prong from moving about said hinge.

8. The spinal implant insertion tool of claim 1, wherein each of said first connectors is a divot defined in a respective first prong or second prong.

9. The spinal implant insertion tool of claim 1, wherein each of said second connectors is a protrusion extending from a respective first prong or second prong.

10. The spinal implant insertion tool of claim 1, wherein each of said first connectors is a divot defined in a respective first prong or second prong and wherein each of said second connectors is a protrusion extending from a respective first prong or second prong.

11. A spinal implant insertion tool comprising:
    a handle portion formed by a proximal end of a first prong and a proximal end of a second prong;
    an attachment portion formed by a distal end of said first prong and a distal end of said second prong;
    a hinged portion positioned between said handle portion and said attachment portion, wherein said first prong and said second prong are coupled by a hinge in said hinged portion;
    a first attachment section of said attachment portion including first connectors configured to hold a spinal plate, wherein one of said first connectors is positioned on said first prong and another of said first connectors is positioned on said second prong;
    a second attachment section of said attachment portion including second connectors configured to hold a spinal cage, wherein one of said second connectors is positioned on said first prong and another of said second connectors is positioned on said second prong;
    a hinge axis defined along said second prong and through said hinge;
    a spinal implant axis defined through a center of the spinal plate and a center of the spinal cage when the spinal plate is held in said first attachment section and the spinal cage is held in said second attachment section; and
    wherein said hinge axis and said spinal implant axis are spaced from each other so that said hinge axis is offset from said spinal implant axis.

12. The spinal implant insertion tool of claim 11, wherein in the hinged portion, said first prong extends at an oblique angle with respect to the proximal end of said first prong and the distal end of said first prong.

13. The spinal implant insertion tool of claim 11, wherein the proximal end of said first prong is parallel to the distal end of said first prong.

14. The spinal implant insertion tool of claim 11, wherein said second prong is linear between its proximal and distal ends.

15. The spinal implant insertion tool of claim 11, further comprising:
a locking collar attached to said handle portion, wherein said locking collar is configured to prevent said first prong and said second prong from moving about said hinge when said locking collar engages both said first prong and said second prong.

16. The spinal implant insertion tool of claim 11, further comprising:
a head attached to said first prong at an end of said handle portion, wherein said head has a greater width than a width of said first prong.

17. The spinal implant insertion tool of claim 11, further comprising:
a serrated ratchet closure positioned on said handle portion, wherein said serrated ratchet closure includes a first latch attached to said first prong and a second latch attached to said second prong; and
wherein said first latch and said second latch are configured to interlock when in contact to prevent said first prong and said second prong from moving about said hinge.

18. The spinal implant insertion tool of claim 11, wherein each of said first connectors is a divot defined in a respective first prong or second prong.

19. The spinal implant insertion tool of claim 11, wherein each of said second connectors is a protrusion extending from a respective first prong or second prong.

20. A spinal implant insertion tool comprising:
a handle portion formed by a proximal end of a first prong and a proximal end of a second prong;
an attachment portion formed by a distal end of said first prong and a distal end of said second prong;
wherein said first prong is not continuously linear between its proximal and distal ends, and wherein said second prong is entirely linear between its proximal and distal ends;
a hinged portion positioned between said handle portion and said attachment portion,
wherein said first prong and said second prong are coupled by a hinge in said hinged portion;
a first attachment section of said attachment portion including first connectors configured to hold a spinal plate, wherein one of said first connectors is positioned on said first prong and another of said first connectors is positioned on said second prong; and
a second attachment section of said attachment portion including second connectors configured to hold a spinal cage, wherein one of said second connectors is positioned on said first prong and another of said second connectors is positioned on said second prong;
wherein said first attachment section is configured to simultaneously hold the spinal plate as said second attachment section holds said spinal cage.

* * * * *